United States Patent [19]
Kubo

[11] Patent Number: 6,146,654
[45] Date of Patent: *Nov. 14, 2000

[54] ADHESIVE MEDICAL COMPOSITION WITH SUSTAINED MEDICAMENT RELEASBILITY AND PROCESS FOR PREPARING SAME

[75] Inventor: Takabumi Kubo, Funabashi, Japan

[73] Assignee: Alcare Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/870,784

[22] Filed: Jun. 6, 1997

[30] Foreign Application Priority Data

Jun. 10, 1996 [JP] Japan ................................. 8-168725

[51] Int. Cl.[7] ........................................... A61F 13/00
[52] U.S. Cl. ..................... 424/443; 424/445; 424/447; 424/448
[58] Field of Search ................................ 424/401, 430, 424/468, 448, 434, 435, 436, 437, 443, 445, 447

[56] References Cited

U.S. PATENT DOCUMENTS 4,551,490  11/1985  Doyle et al. ............................. 524/22

*Primary Examiner*—Thurman K. Page
*Assistant Examiner*—S. Howard
*Attorney, Agent, or Firm*—Haverstock, Garrett & Roberts

[57] ABSTRACT

The present invention is directed to a blending medical composition with a sustained medicament releasability, which can reduce the amount of medicament required to be contained in the composition, and can control the amount of medicament to be released according to a degree of moisture present at a moist application site. The present composition includes a medicament-containing hydrophilic composition including a water-soluble or water-dispersible hydrophilic composition and a medicament, dispersed and blended into a binding composition capable of retaining the medicament-containing hydrophilic composition.

18 Claims, 1 Drawing Sheet

ADHESIVE MEDICAL COMPOSITION WITH SUSTAINED MEDICAMENT RELEASBILITY AND PROCESS FOR PREPARING SAME

The present invention relates to a blending medical composition with a sustained medicament releasability, which is useful for keeping continuously active for a long time an ingredient having a useful pharmacological action, such as an action to promote wound healing, an analgesic action, an action to lessen inflammation, an antibacterial action against harmful bacteria to living bodies, etc. at living body sites, where there is production of moisture or water-containing exudate, such as sweat, or those from wounds or injuries such as, for example, decubitus, burn injury, below-knee ulcers, peeling, operative wounds, cuts, abrasions, etc.; and oral secretion, excreta from stomas, fistulas, etc.

BACKGROUND OF THE INVENTION

One known sustained release technique for ingredients having a pharmacological action, for example, wound-healing promoters, antibacterial agents, anti-inflammatory agents, etc., that is, ingredients having an action to promote wound healing, an analgesic action, an action to lessen inflammation, an antibacterial action against harmful bacteria to living bodies, etc., is to blend such an ingredient into a tackifying base. A similar sustained release technique is a DDS (drug delivery system) technique which is widely used with ointments, pastes, liniments and lotions The basic concept of this technique is the blending of a medicament into a tackifying base, where the medicament diffuses through the base to reach the skin boundary. Then, distribution of the medicament from the base to the skin surface takes place, and the medicament is transferred into the living body by diffusion through the skin tissues to act on the target organ. This sustained medicament release principle is based on a technique wherein the desired diffusion rate of a medicament through the base is achieved by selecting a base composition and designing a diffusion promoter, etc. for the base composition. In the application phase, however, the diffusion rate is also temperature dependent and thus these techniques are not suitably applicable to moisture-rich sites.

As a medical tackifying composition with a sustained medicament releasability directed to the application to moisture-rich sites, Japanese Examined Patent Application Publication No. Sho 44-16676 teaches an oral patch material for oral treatment, which comprises a hydrophobic elastomer blended with a hydrophilic hydrocolloid, and also discloses that the patch material is suitable for application to moisture-rich diseased parts and can be kept in a tackified state for a long time as a skin-binding patch for stomas and dressing for wounds in addition to usage as oral treating patch materials. The disclosure further states that it is possible to blend a medicament into a tackifier containing a hydrocolloid ingredient.

U.S. Pat. No. 4,340,043 discloses an adhesive-coated sheet material for wound covering, which comprises 1 to 25% by weight of an antibacterial agent to kill bacteria in wounds and surrounding covered skin area, a metal salt; an antibiotic such as neomycin; chlorobexidine and its salts; a quaternary ammonium compound; idophor; silversulphadiazine; or the like, and further discloses that the required content of the antibacterial agent is preferably up to 15% in a finely divided form to give an antibacterial action.

U.S. Pat. No. 4,551,490 discloses a pressure sensitive adhesive composition for various medical applications, which is resistant to erosion by moisture and biological fluids, which comprises a blend of mineral oil, one or more polyisobutylenes, or mixtures of one or more polyisobutylenes and an elastomer such as butyl rubber, styrene radical or block type copolymers, water-soluble hydrocolloid gums, water-swellable cohesive strengthening agents, tackifiers, etc., and also discloses such an active ingredients as silver sulphadiazine, where other silver compounds may be contained in the pressure-sensitive adhesive composition as a bandage for burn wounds.

Japanese Unexamined Patent Application Publication No. Hei 2-147063 discloses an antibacterial tackifying composition, which comprises a tackifying mixture of a solid hydrophobic acryl-based tackifier, an antibacterially effective amount of silver sulphadiazine, and such an effective amount of internally cross-linked sodium carboxymethyl cellulose as to release the silver sulphadiazine from the tackifying mixture, and further discloses that incorporation of the internally cross-linked sodium carboxymethyl cellulose into the acryl-based tackifier can promote the antibacterial effect with a surprisingly small amount of silver sulphadiazine.

However, all the above-mentioned techniques are based on mere blending of a medicament in a tackifying composition as a base to obtain a sustained medicament releasability by adjusting the amount of a medicament to be mixed or changing the constitutions of the tackifying composition. An increased amount of the medicament to be mixed for strengthening the physiological action inevitably entails problems of medicament side effect and cost increase. Changing the constitutions of tackifying compositions also has a limit to combinations of medicaments to be used and applicability to moist sites.

SUMMARY OF THE INVENTION

The present invention has been established to overcome the above-mentioned disadvantages of the prior art and to provide a blending medical composition with a sustained medicament releasability, which contains a decreased amount of a medicament and can control a medicament releasing rate by a moisture degree when applied at moist sites.

According to one aspect of the present invention, a medicament-containing hydrophilic composition comprising a water-soluble or water-dispersible hydrophilic composition and a medicament is dispersed and blended into a binding composition capable of retaining the medicament-containing hydrophilic composition within.

According to another aspect of the present invention, the medicament-containing hydrophilic composition with sustained medicament releasability is prepared by uniformly mixing a hydrophilic composition and a medicament with a moisture or a water soluble binder in either powdered or moist form, and dispersing and blending the medicament-containing hydrophilic composition into a binding composition.

In use, the present blending medical composition will release the medicament from the hydrophilic composition upon absorption of moisture, humor, etc. from living bodies, and thus the medicament is effectively releasable from the hydrophilic composition according to the degree of moisture, humor, etc. present at sites to which the blending medical composition is applied. That is, the contained medicament can be very efficiently utilized, resulting in saving of the amount of medicament to be contained in the blending medical composition and also in eliminating of a side effect risk due to an action of the medicament, when contained in excess, for a short time. Furthermore, no pharmacological action takes place at normal sites where moisture, humor, etc. exude and secrete less, causing no side effect at all. Thus, the present blending medical composition can be safely used with a remarkable cost reduction effect.

DETAILED DESCRIPTION OF SEVERAL PREFERRED EMBODIMENTS

Figure 1:
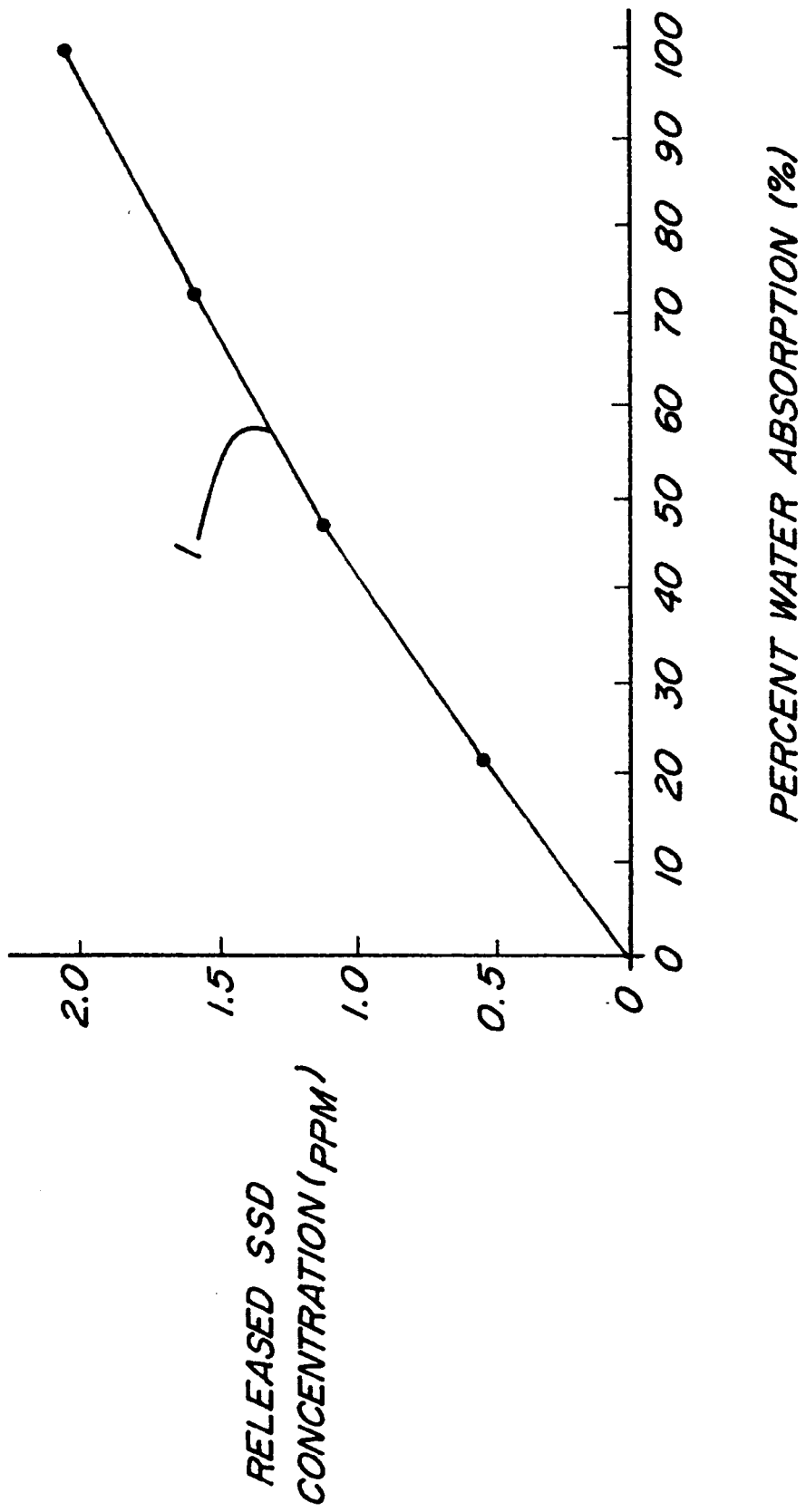
FIG. 1 is a diagram showing the relation between released SSD concentration and present water absorption according to the present invention.

Water-soluble or water-dispersible hydrophilic compositions for use in the present invention can include inorganic or organic natural, semi-synthetic and synthetic water-soluble or water-dispersible solid ingredients. Solid ingredients reactive with the medicament are not preferable. Water-soluble or water-dispersible solid ingredients for use in the present invention may include, for example, neutral or weakly acidic inorganic compounds such as titanium oxide, zinc oxide, silica, boric acid, etc.; vegetable mucilagos such as carrageenan, gum arabic, karaya gum, gear gum, psyllium seed gum, tragacanth gum, pectin, etc.; marine algae extracts cuh as alginate, agar, etc.; cellulose such as carboxymethyl cellulose, carboxyethyl cellulose, etc.; natural, semi-synthetic and synthetic water-soluble polymers or their modified polymers such as polyvinyl alcohol, sodium polyacrylate, polyethylene oxide, polyvinylpyrolidone, etc. alone or their mixtures.

When the medicament is added to the hydrophilic composition, it is possible to further add thereto fine water-insoluble powders, which are unreactive with the medicament and harmless to living bodies so as to make the medicament dispersibility higher. As a water-soluble binder for integrating these ingredients, a viscous hydrophilic composition can be used among the above-mentioned hydrophilic compositions. Preferably, water-soluble tackifiers such as vegetable mucilages having a high viscosity, proteins, semi-synthetic and synthetic water-soluble polymers or their modified polymers, or vinyl acetate, gum arabic, or the like can be used.

Any binding composition can be used, so long as it is unreactive with the water-soluble or water-dispersible hydrophilic composition, it is capable of retaining the hydrophilic composition within upon binding, and it keeps a desired shape without disintegration by contact with moisture or humor. Well known medical binding compositions can be used. Various binding compositions such as rubber-based, acryl-based, urethane-based, silicone-based, polyvinyl ether-based or similar based compositions can be used.

The binding compositions can be classified into three major types: (A) a binding composition comprising a hydrophobic ingredient alone, (B) a binding composition comprising a mixture of a hydrophobic ingredient and a hydrophilic ingredient, and (C) a binding composition comprising a hydrophilic ingredient alone. Any one of these three types can be used.

As type (A) binding compositions, any one of a rubber-based, acryl-based, urethane-based, silicone-based, polyvinyl ether-based and similar binding compositions can be used. The rubber-based binding composition comprises an elastomer such as polyisoprene, natural rubber, polyisoprene, nitrile rubber, styrene-butadiene rubber, styrene-isoprene-styrene rubber, styrene-butadiene-styrene rubber, styrene-polyethylene/polybutylene-styrene rubber, etc. as the main ingredient and further contains, if desired, a tackifier such as polyterpene resin, gum rosin, rosin ester, oily phenol resin, cumarone-indene resin, petroleum-based hydrocarbon resin, etc.; a softener such as mineral oil, liquid polybutene, liquid polyacrylate, vaseline, lanolin, etc.; a filler such as zinc oxide, talc, silica, aluminum hydroxide, calcium carbonate, etc.; an age resistor; a pigment; and the like. The acryl-based, urethane-based, silicon-based and polyvinyl ether-based binding compositions are prepared upon selection of monomer species and degree of polymerization so as to obtain approximate initial adhesion and adhesive retention at preparation stages of the respective binding compositions. Several kinds of the resulting compositions can be blended together, when required. In case of the acryl-based compositions, various species of acrylic acid derivatives such as methyl acrylate, ethyl acrylate, 2-ethylhexyl acrylate, methyl methacrylate, butyl acrylate, etc. on other monomers such as vinyl acetate, etc. can be used for polymerization. These monomers can be polymerized independently and the resulting individual polymers can be blended.

Type (B) binding compositions can comprise a mixture of rubber-based, acryl-based, urethane-based, silicone-based, polyvinyl ether-based or similar binding composition of type (A) with a water-soluble polymer. The water-soluble polymer can include the natural, semi-synthetic or synthetic water-soluble polymers or their modified polymers used in the above-mentioned hydrophilic composition, preferably those having a relatively high molecular weight. Generally from about 20 to about 70% by weight of the water-soluble polymer is contained in the hydrophobic rubber-based, acryl-based, urethane-based, silicone-based, polyvinyl ether-based or similar binding composition.

Type (C) binding compositions are based on incorporation of hydroxyl groups into the acrylic-based, urethane-based, silicone-based, or polyvinyl ether-based polymer. Water absorbing characteristics and the water-absorbed state of the binding compositions of type (C) can be adjusted by adjusting a proportion of the hydroxyl group to be incorporated into the polymers or a proportion of a cross-linking agent to be added.

Among types (A), (B) and (C) binding compositions, compositions of types (B) and (C) having a water absorbability are preferable.

Any of the binding compositions of solvent type or non-solvent type can be used. Preferable is the non-solvent type, which ensures that the surface of the medicament-containing hydrophilic composition is hardly covered with the binding composition. That is, complete covering of the hydrophilic composition in the binding composition with the binding composition can block moisture passages from the outside, resulting in a decrease in the water absorbability of the hydrophilic composition. The non-solvent type ensures appropriate formation of moisture passages from the surface to the hydrophilic composition, through which the hydrophilic composition can absorb moisture or humor to undergo dissolution, dispersion or swelling, and thus can be exposed to the body surface to place the contained medicament into action.

A preferred example of the binding composition is a medical tackifying composition comprising a pressure sensitive tackifying component consisting of a thermoplastic elastomer, an elastomer having a low compatibility with the thermoplastic elastomer, a softener containing at least a liquid rubber and a tackifier; and a water-absorbable component, such as previously proposed by the present applicant in Japanese Patent Application No. Hei 7-129507. In relation to that, a binding composition comprising a pressure sensitive natural or synthetic tackifying rubber containing a thermoplastic elastomer and a water-soluble hydrocolloid rubber, a binding composition comprising polyisobutylene as the main ingredients, admixed with butyl rubber, styrene-butadiene-styrene block copolymer, and mineral oil, a tackifier, a water-swellable cohesive strengthening agent, etc. and a hydrocolloid rubber, as disclosed in Japanese Unexamined Patent Application Publication Nos. Sho 58-103452, Sho 60-20976, Hei 3-92153, Hei 5-123389, Hei 6-200, etc., can be used.

Medicaments that are unreactive with the hydrophilic composition and have a proper effect without denaturing, even upon the action of moisture, such as an antibacterial agent, a bactericide, an antibiotic, an analgesic, an anti-inflammatory agent, a wound healing-promoter, a block coagulant, a local anesthetic, etc. for example, silver sulphodiazine (as will be hereinafter referred to as SSD), iodine, zeolite, cyconin, fradiomycin sulfate, gentamicin sulfate, erythromycin, chlorohexidine gluconate, benzalkonium chloride, dl-camphor, lidocaine, procaine hydrochloride, diphenhydramine, a bacterial skin disease-curing agent "Exalbe (*Lactobacillus casei*)", insulin, etc. can be used.

The present blending medical composition with a sustained medicament releasability can be prepared, for example, according to the following procedure: a medicament and a hydrophilic composition are mixed together under a moist condition to obtain a moisture-containing, viscous sticky medicament-containing hydrophilic composition, and the resulting composition is dried in such an atmosphere as not to denature the ingredients, and ground to appropriate powder (grains). Then, the powdery grains are mixed into a binding composition comprising a rubber elastomer, a softener, a tackifier, a filler, etc. or a binding composition comprising an acrylic acid ester, urethane, silicon, etc. as the main ingredients to obtain a blending medical composition with a sustained medicament releasability.

According to another procedure, relatively fine powders of a medicament and a hydrophilic composition were homogeneously mixed together and then admixed with a moisture or a water-soluble binder to obtain an integrated mixture of the medicament and the hydrophilic composition. The medicament-containing hydrophilic composition, after made into appropriate sizes, is mixed into a binding composition comprising a rubber elastomer, a softener, a tackifier, a filler, etc. as the main components, to obtain a blending medical composition with a sustained medicament releasability.

In the present invention, a physiologically active medicament is physically enclosed into a water-soluble or water-dispersible hydrophilic composition, and thus, upon dissolution or dispersion of the hydrophilic composition by a water-containing liquid such as an exudate, secretion, excreta, etc. from living bodies, the medicament is readily released from the hydrophilic composition and acts directly on the living bodies. Furthermore, the hydrophilic composition is dispersed in the binding composition while retaining the water absorbability, and upon absorption of a water-containing liquid such as an exudate, secretion, excreta, etc. from living bodies, the hydrophilic composition starts to undergo dissolution, separation, decomposition, etc. and is exposed to the outside surface of the blending medical composition with a sustained releasability. Furthermore, the swelling of the hydrophilic composition causes a portion of the hydrophilic composition to reach the outside surface of the composition, whereby the medicament is placed into the effective action. Once the hydrophilic composition absorbs moisture or humor, the water-absorbed hydrophilic composition causes the moisture or humor to diffuse through gaps in the hydrophilic composition, resulting in successive dissolution, separation and decomposition of the hydrophilic composition to expose the hydrophilic composition to the outside surface of the medical composition by exudation or pushing, and thus the physiological action of the medicament can be obtained according to the moisture degree.

Furthermore, in the present invention, the hydrophilic composition is exposed to the body surface by its dissolution, decomposition, separation, swelling, etc. due to the water absorption, and thus the hydrophilic composition is not exposed to the body surface where there is no or less water-containing liquid such as an exudate, secretion. excreta, etc. from living body, and thus no side effect is observable.

EXAMPLES

The present invention will be described below, referring to Examples.

Example 1

About 1.7 parts by weight of pharmacopoeia grade silver sulphadiazine (as hereinafter referred to as SSD) as an antibacterial agent and about 9.5 parts by weight of pectin of citrus origin as a hydrophilic composition were mixed together and admixed with ethanol and purified water with stirring to obtain a homogeneous mixture, followed by drying in hot air at from about 70° to about 100° C. The dried mixture was ground to particle sizes of about 60 to about 150 mesh in a pulverizer to obtain a hydrophilic composition. Separately, about 21 parts by weight of Europren SOLT 190 made by Eni Chem Co., Ltd., about 14 parts by weight of Kurapren LIR 30 made by Kuraray Isoprene Chemical Co., Ltd., about 28 parts by weight of Himol 5H (polyisobutylene) made by Nippon Petrochemical Co., Ltd., about 7 parts by weight of Exxon Butyl (Butyl 268) made by Exxon Co., Ltd., about 15 parts by weight of Arcon P100 made by Arakawa Chemical Co., Ltd., and about 8 parts by weight of KE 311 were thoroughly kneaded, and further admixed with a filler ingredient prepared by mixing about 8 parts by weight of CMC 1380 made by Daicel Chemical Co., Ltd., about 25 parts by weight of karaya gum (about 150 mesh), about 35 parts by weight of gelatin and about 2 parts by weight of Nipseal VN-3 made by Nippon Silica Industry Co., Ltd., followed by stirring to obtain a homogenous mixture. Finally, the first hydrophilic composition was added to the second mixture with stirring to obtain a homogeneous mixture. Thereby the present blending medical composition was obtained.

Examples 2 through 7

Examples 2 through 7 of additional blending medical compositions according to the present invention were prepared in the same manner as in Example 1, using different ingredients as shown in Tables 1 and 2.

TABLE 1

| Item | | Ingredients | | Example 1 | Example 2 | Example 3 | Example 4 | Example 5 |
|---|---|---|---|---|---|---|---|---|
| Medicament-containing hydrophilic composition | Water-soluble hydrophilic composition | Pectin | Citrus origin | 9.5 | 15 | 10 | | 10 |
| | | CMC | CMC 1380 (Daicel) | | 27.8 | | 20 | |
| | | Zinc Oxide | Pharmacopoeia | | | | | |
| | | Karaya Gum | 150 meshes | | | 16.3 | 40 | 10 |
| | | Gelatin | | 4.2 | | | | |
| | Medicament | SSD | | 1.7 | 1.1 | 1.1 | 1 | 1 |
| Binding Composition | Hydrophobic pressure-sensitive tackifier | Polyisobutylene | Himol 4H | | 31 | | | |
| | | | Himol 5H | | 8.9 | | | |
| | | Butyl rubber | Butyl 268 | | 4.4 | | | |
| | | Petroleum-based resin | | | | | | |
| | | Silica | Nipseal VN-3 | | 8.2 | | | |
| | | Acrylic acid ester-based | Binsol R-550 (Ipposha) | | | | 60 | |
| | | Silicon-based tackifier | | | | | | 70 |
| | Mixed pressure-sensitive tackifier of hydrophobic ingredients and hydrophilic ingredients | Polyisobutylene | Himol 5H | 28 | | | | |
| | | Butyl rubber | Butyl 268 | 7 | | | | |
| | | SIS | Europren SOLT190 | 21 | | | | |
| | | Liquid rubber | LIR30 | 14 | | | | |
| | | Resin | Arcon P-100 | 15 | | | | |
| | | | KE 311 | 8 | | | | |
| | | CMC | CMC1380 | 8 | | | | |
| | | Karaya gum | 150 mesh | 24 | | | | 40 |
| | | Gelatin | | 35 | | | | |
| | | Silica | Nipseal VN-3 | 2 | | | | |
| | | Acrylic acid ester-based | Binsol R-550 (Ipposha) | | | | | 50 |
| | | Pectin | | | | | | |
| | Hydrophilic pressure sensitive tackifier | Acryl-based ※1 | | | | | | |
| | | Urethane-based ※2 | | | | | | |

TABLE 2

| Item | | Ingredients | | Example 6 | Example 7 | Example 8 | Example 9 | Comparative Example 1 | Comparative Example 2 |
|---|---|---|---|---|---|---|---|---|---|
| Medicament-containing hydrophilic composition | Water-soluble hydrophilic composition | Pectin | Citrus origin | 10 | 10 | 9.5 | 9.5 | | |
| | | CMC | CMC 1380 (Daicel) | | | | | | |
| | | Zinc Oxide | Pharmacopoeia | | | | | | |
| | | Karaya Gum | 150 meshes | | | | | | |
| | | Gelatin | | | | | | | |
| | Medicament | SSD | | 1.1 | 1 | 0.52 | 0.86 | 1.7 | 1 |
| Binding Composition | Hydrophobic pressure-sensitive tackifier | Polyisobutylene | Himol 4H | | | | | | |
| | | | Himol 5H | | | | | | |
| | | Butyl rubber | Butyl 268 | | | | | | |
| | | Petroleum-based resin | | | | | | | |
| | | Silica | Nipseal VN-3 | | | | | | |
| | | Acrylic acid ester-based | Binsol R-550 (Ilposha) | | | | | | |
| | | Silicon-based tackifier | | | | | | | |
| | Mixed pressure-sensitive tackifier of hydrophobic ingredients and hydrophilic ingredients | Polyisobutylene | Himol 5H | | | | | | |
| | | Butyl rubber | Butyl 268 | | | 7 | 7 | 7 | |
| | | SIS | Europren SOLT190 | | | 21 | 21 | 21 | |
| | | Liquid rubber | LIR30 | | | 14 | 14 | 14 | |
| | | Resin | Arcon P-100 | | | 15 | 15 | 15 | |
| | | | KE 311 | | | 8 | 8 | 8 | |
| | | CMC | CMC1380 | | | 8 | 8 | 8 | |
| | | Karaya gum | 150 mesh | | | 25 | 25 | 25 | |
| | | Gelatin | | | | 35 | 35 | 35 | |
| | | Silica | Nipseal VN-3 | | | 2 | 2 | 2 | |
| | | Acrylic acid ester-based | | | | | | | |

TABLE 2-continued

|  |  | Example |  |  |  | Comparative Example |  |
|---|---|---|---|---|---|---|---|
| Item | Ingredients | 6 | 7 | 8 | 9 | 1 | 2 |
| Hydrophilic pressure- sensitive tackifier | (Ipposha) Pectin Acryl-based ※1 Urethane-based ※2 | 100 | 100 |  |  | 9.5 | 100 |

In Tables 1 and 2 ※1 is a hydrophilic acryl-based binder obtained by synthesizing acrylic acid ester as a polymer ingredient from about 45 parts by weight of 3-(methacrylamide) propyltrimethylammonium chloride and about 55 parts by weight of butyl acrylate in ethyl alcohol and water in a ratio of about 90:10, while adding a 2 wt % catalyst solution in ethyl acetate and ethyl alcohol containing azobisisobutyronitrile as a polymerization catalyst in a proportion of about 0.6% by weight to the total weight of the above-mentioned monomers with stirring at about 65° C. in an inert gas atmosphere until the apparent viscosity reached about 10,000 cps, and further by adding thereto about 50 parts by weight of diglycerine per 100 parts by weight of the polymer ingredient.

In Tables 1 and 2, ※2 is an urethane-based hydrophilic binder obtained by conducting reaction of polyurethane prepolymer with about 433 g of polyether glycol having an average molecular weight of about 2,000, obtained by addition of polyethylene oxide (PO) to polypropylene glycol, and about 433 g of polyethertriol having an average molecular weight of about 4,000, obtained by addition of PO to glycerin, together with about 133g of toluene diisocyanate (TDI) at about 80° C. for about 8 hours to obtain a second polyurethane prepolymer containing an isocyanate group (NCO) of 3.19%, while mixing about 1,000 g of polyethertriol having an average molecular weight of about 2,000, obtained by addition of PO to glycerin, with about 5 g of zinc octanoate to obtain a curing agent, and then by mixing about 200 g of the second polyurethane prepolymer with about 101.2 g of the curing agent with stirring.

Comparative Example 1

About 21 parts by weight of Europren SOLT 190 made by Eni Chem Co., Ltd., about 14 parts by weight of Kurapren LIR 30 made by Kuraray Isoprene Chemical Co., Ltd., about 28 parts by weight of Himol 5H (polyisobuytlene) made by Nippon Petrochemical Co., Ltd., about 7 parts by weight of Exxon Butyl (Butyl 268) made by Exxon Co., Ltd., about 15 parts by weight of Arcon P100 made by Arakawa Chemical Co., Ltd., and about 8 parts by weight of KE 311 were kneaded in a pressure kneaded, and, when fully mixed, further admixed with a filler ingredient obtained by mixing about 8 parts by weight of CMC 1380 made by Daicel Chemical Co., Ltd., about 25 parts by weight of karaya gum (150 mesh), about 35 parts by weight of gelatin, about 2 parts by weight of Nipseal VN-3 made by Nippon Silica Industry Co., Ltd., about 9.5 parts by weight of pectin, and about 1.7 parts by weight of SSD, followed by stirring to obtain a homogeneous mixture. Thereby a comparative blending medical composition was obtained.

Comparative Example 2

Another comparative blending medical composition was prepared in the same manner as in Comparative Example 1 by using different ingredients as shown in Table 2.

Preparation of Test Samples:

Test samples were made in the following manner: Blending compositions of Examples and Comparative Examples were placed in a thermostat at 60° to 90° C. to soften the compositions at a thoroughly uniformed temperature, and then the softened compositions were each sandwiched between 2 release papers to prevent adhesion, and pressed in a press to sheets having a thickness of about 1 mm, from which test samples, 5 cm×5 cm, were made.

Determination of Amounts of Released Medicament 1:

Test samples, 1 mm thick and 5 cm×5 cm in size, of Examples and Comparative Examples were left standing each in about 30 ml of physiological saline solution at about 37° C. for 72 hours to extraction, and then the test samples were washed with physiological saline solution. The total amount of the physiological saline solution containing the released medicament was made about 100 ml, and about 10 ml of 28% ammonia water was added thereto. Measurement was made each for 110 ml of the test solution by an atomic absorption spectrometer and released SSD concentrations were calculated from the measurement data using the following formula:

$$x = \frac{\gamma(V/C)}{F}$$

where:

x=released SSD concentration

γ=measurement data of the Spectrometer (Ag concentration of the test solution)

V=amount of test solution (110 ml in this case)

C=Ag content in SSD (0.3 in this case)

F=surface area of the test sample (2500 mm$^2$ in this case)

The results are shown in Table 3, from which it is evident that in the Examples the medicament was released in amounts about 10 to about 100 times as great as those of the Comparative Examples.

TABLE 3

| Released SSD concentration (ppm) | |
|---|---|
| Example 1 | 40.67 |
| Example 2 | 43.81 |
| Example 3 | 37.44 |
| Example 4 | 29.51 |
| Example 5 | 38.30 |
| Example 6 | 22.74 |
| Example 7 | 26.03 |
| Example 8 | 2.67 |
| Example 9 | 9.65 |

TABLE 3-continued

| Released SSD concentration (ppm) | |
| --- | --- |
| Comparative Example 1 | 0.55 |
| Comparative Example 2 | 0.31 |

Determination of Amounts of Released Medicament 2:

To observe relations between percent water absorption and released SSD concentration, test samples, 1 mm thick and 5 cm×5 cm in size, containing about 0.05% by weight of SSD, other ingredients being the same and in the same amounts as in Example 1, were used. The test samples were left standing in about 30 ml of physiological saline solution at about 37° C. and picked tip at each stage at which the weights of physiological saline solution absorbed by the test samples amounted to about 20, 50, 70 and 100% of the weights of the original test samples, respectively (by setting the pickup times on the basis of results of water absorption test made beforehand), and the surfaces of the picked-up test samples were washed with physiological saline solution at each pickup time. Total amount of the physiological saline solution containing the released medicament was made about 100 ml and about 10 ml of 28% ammonia water was added thereto. Measurement was made each for 110 ml of the test solution by an atomic absorption spectrometer, and released SSD concentrations against percent water absorption were calculated from the measurement data. The results are shown in Table 4.

TABLE 4

| Percent water absorption (%) | 0 | 21 | 47 | 72 | 99 |
| --- | --- | --- | --- | --- | --- |
| Released SSD concentration (ppm) | 0 | 0.59 | 1.13 | 1.57 | 2.05 |

The results were plotted in a diagram as shown in FIG. 1. As is evident from Curve 1 of FIG. 1, the relation of released SSD concentration to percent water absorption was substantially linear, and an ideal sustained medicament release characteristic was obtained.

Thus, there has been shown and described a novel method and composition for blending medical composition with sustained medicament releasability which fulfill all the objects and advantages sought therefor. It would be apparent to those skilled in the art, however, that many changes, variation, modification, and other uses and applications for the subject method and composition are possible, and also such changes, variations, modifications, and other uses and applications which do not depart from the spirit and scope of the invention are deemed to be covered by the invention which is limited only by the claims which follow.

What is claimed is:

1. An adhesive composition with a sustained medicament releasability, comprised of a medicament, a hydrophilic composition, and a binding composition capable of retaining the hydrophilic composition, said hydrophilic composition being soluble in water, humor and exudate, and being selected from the group consisting of natural hydrophilic compositions, semi-synthetic hydrophilic compositions and synthetic hydrophilic compositions and mixtures thereof, said medicament being dispersed and blended into said hydrophilic composition to form a medicament-containing hydrophilic composition, and particles of said medicament-containing hydrophilic composition being dispersed in said binding composition, wherein a portion of said medicament-containing hydrophilic composition particles is capable of being exposed to an outside surface of said binding composition by dissolution, separation or decomposition of said medicament-containing hydrophilic composition particles by absorption of a water-containing liquid, to release said medicament from said portion of said medicament-containing hydrophilic composition particles.

2. An adhesive composition with a sustained medicament releasability according to claim 1, wherein the hydrophilic composition is unreactive with the medicament and is soluble in water, humor, exudate, and mixtures thereof.

3. An adhesive composition with a sustained medicament releasability according to claim 2, wherein the hydrophilic composition is comprised of a filler material selected from the group consisting of natural fillers, semi-synthetic fillers, synthetic fillers, and mixtures thereof.

4. An adhesive composition with a sustained medicament releasability according to claim 1, wherein the hydrophilic composition has a bindability characteristic.

5. An adhesive composition with a sustained medicament releasability according to claim 2, wherein the hydrophilic composition is bound by a water-soluble binder.

6. An adhesive composition with a sustained medicament releasability according to claim 1, wherein the binding composition is an elastomer-based composition which coexists with the hydrophilic composition, and is more hydrophobic and resistant to disintegrative action than the hydrophilic composition, even upon absorption of water, humor or exudate by at least the hydrophilic composition.

7. An adhesive composition with a sustained medicament releasability according to claim 1, wherein the binding composition is a pressure-sensitive tackifying composition.

8. An adhesive composition with a sustaining medicament releasability according to claim 7, wherein the pressure sensitive tackifying composition is selected from the group consisting of rubber based compositions, acryl-based compositions, urethane-based compositions, silicone-based compositions, polyether-based compositions, and combinations thereof.

9. An adhesive composition with a sustained medicament releasability according to claim 1, wherein the medicament-containing hydrophilic composition contains an amount of the medicament sufficient for showing a useful pharmacological action on living bodies, where the medicament and hydrophilic composition coexist in such a combination as to release the medicament from the medicament-containing composition upon absorption of water, humor, or exudate.

10. A process for preparing an adhesive composition with a sustained medicament releasability, comprising the steps of:

(a) uniformly mixing a hydrophilic composition and a medicament to form a medicament-containing hydrophilic composition so that the medicament is physically enclosed into the hydrophilic composition then grinding the medicament-containing hydrophilic composition into particles; and then (b) uniformly mixing the particles of the medicament-containing hydrophilic composition with a moisture-soluble or a water-soluble binder so that the particles of the medicament-containing hydrophilic composition are dispersed in the binder.

11. A process for preparing an adhesive composition with a sustained medicament releasability according to claim 10, where in step (a) the medicament-containing hydrophilic composition is dried prior to said grinding to form the particles of the medicament-containing hydrophilic composition.

12. A process for preparing an adhesive composition with a sustained medicament releasability according to claim 11, wherein the dried medicament-containing hydrophilic composition is ground to form the particles so as to have particle sizes of from about 60 to about 150 mesh.

13. A process for preparing an adhesive composition with a sustained medicament releasability according to claim 11, where in step (a) the medicament-containing hydrophilic composition and the medicament are mixed with at least one liquid so as to be in a moist condition prior to being dried.

14. A process for preparing an adhesive medical composition with a sustained medicament releasability according to claim 10, wherein the hydrophilic composition is comprised of a filler material selected from the group consisting of natural fillers, semi-synthetic fillers, synthetic fillers, and combinations thereof.

15. A process for preparing an adhesive medical composition with a sustained medicament releasability according to claim 10, wherein the binding composition is selected from the group consisting of a hydrophilic pressure sensitive tackifier, a hydrophobic pressure sensitive tackifier, and a mixture of a hydrophobic pressure sensitive tackifier and a hydrophilic pressure sensitive tackifier.

16. A process for applying an adhesive composition with a sustained medicament releasability to a living body, wherein the process includes the following steps:
   (a) forming the adhesive medical composition with a sustained medicament releasability by uniformly mixing a hydrophilic composition and a medicament in a moist condition to form a hydrophilic composition with the medicament physically enclosed therein, followed by driving and grinding the hydrophilic composition with the medicament physically enclosed therein into particles, followed by uniformly mixing the particles of the hydrophilic composition with the medicament physically enclosed therein with a moisture or a water-soluble binder so that the medicament-containing hydrophilic composition particles are dispersed in the binder to form the adhesive composition with a sustained medicament releasability;
   (b) applying the adhesive composition with a sustained medicament releasability to a portion of a living body in contact with moisture; and,
   (c) leaving the adhesive composition with a sustained medicament releasability in contact with the living body for a sufficient amount of time to absorb at least some moisture from the living body and to release an amount of the medicament in accordance with an amount of the moisture absorbed.

17. An adhesive composition with a sustained medicament releasability, comprising:
   a hydrophilic composition component containing a medicament, and
   an adhesive composition component selected from a group consisting of a hydrophobic pressure sensitive tackifier, a hydrophilic pressure sensitive tackifier, and a mixed pressure sensitive tackifier of hydrophobic ingredients and hydrophilic ingredients,
   wherein the adhesive composition with a sustained medicament releasability is made by a process wherein the medicament and the hydrophilic composition components are mixed in a moist condition to form an integrated mixture, then the integrated mixture is dried and then ground to form a powder, and then the powder is uniformly dispersed in the adhesive composition component, the medicament being physically enclosed in the hydrophilic composition component.

18. An adhesive composition with a sustained medicament releasability, comprising:
   a hydrophilic composition component soluble in water, humor and exudate, said hydrophilic composition component being selected from the group consisting of natural hydrophilic compositions, semi-synthetic hydrophilic compositions and synthetic hydrophilic compositions and mixtures thereof, and said hydrophilic composition component containing a medicament, and
   an adhesive composition component selected from the group consisting of a hydrophobic pressure sensitive tackifier, a hydrophilic pressure sensitive tackifier, and a mixed pressure sensitive tackifier of hydrophobic ingredients and hydrophilic ingredients,
   wherein the adhesive composition with a sustained medicament releasability is made by a process comprising the steps of:
     (a) homogeneously mixing fine powders of the hydrophilic composition component and the medicament, then admixing the mixture of the hydrophilic composition component and the medicament with a moisture soluble binder or a water-soluble binder to obtain an integrated mixture, and
     (b) uniformly mixing the integrated mixture into the binding composition component.

* * * * *

UNITED STATES PATENT AND TRADEMARK OFFICE
CERTIFICATE OF CORRECTION

PATENT NO.: 6,146,654

DATED: November 14, 2000

INVENTOR(S): Takabumi Kubo

It is certified that errors appear in the above-identified patent and that said Letters Patent is hereby corrected as shown below:

Column 1, line 14, "bum" should be --burn--.

Column 1, line 28, after "lotions", insert --.--.

Column 1, line 60, "chlorobexidine" should be --chlorohexidine--.

Column 3, line 23, "gear" should be --guar--.

Columns 7 and 8, delete Table 1 and Table 2 and substitute Table 1 and Table 2 attached hereto.

Column 11, line 15, "tip" should be --up--.

Column 12, line 9, delete "and is soluble in water, humor, exudate, and mixtures thereof".

Column 13, line 30, "driving" should be --drying--.

Signed and Sealed this

First Day of May, 2001

*Attest:*

NICHOLAS P. GODICI

*Attesting Officer*  *Acting Director of the United States Patent and Trademark Office*